(12) United States Patent
Huang et al.

(10) Patent No.: US 8,277,957 B2
(45) Date of Patent: Oct. 2, 2012

(54) QUINOXALINE DERIVATIVES AND ORGANIC LIGHT-EMITTING DIODES COMPRISING THE SAME

(75) Inventors: Heh-Lung Huang, Taipei County (TW); Teng-Chih Chao, Pingjhen (TW); Hao-Chun Lee, Hsinchu (TW)

(73) Assignee: Industrial Technology Research Institute, Hsinchu County (TW)

(*) Notice: Subject to any disclaimer, the term of this patent is extended or adjusted under 35 U.S.C. 154(b) by 167 days.

(21) Appl. No.: 12/869,899

(22) Filed: Aug. 27, 2010

(65) Prior Publication Data

US 2011/0049495 A1 Mar. 3, 2011

(30) Foreign Application Priority Data

Aug. 28, 2009 (TW) .............................. 98129006 A
Jul. 23, 2010 (TW) .............................. 99124279 A

(51) Int. Cl.
*H01L 51/54* (2006.01)
*C07D 241/42* (2006.01)
*C07D 403/14* (2006.01)
*C07D 401/14* (2006.01)
*C07D 417/14* (2006.01)

(52) U.S. Cl. ........ 428/690; 428/917; 313/504; 313/506; 544/353; 544/296

(58) Field of Classification Search .................. None
See application file for complete search history.

(56) References Cited

U.S. PATENT DOCUMENTS

| | | |
|---|---|---|
| 2007/0015003 A1 | 1/2007 | Hwang et al. |
| 2007/0176544 A1 | 8/2007 | Koike et al. |
| 2008/0099758 A1 | 5/2008 | Lee et al. |
| 2008/0193794 A1 | 8/2008 | Egawa et al. |
| 2008/0217608 A1 | 9/2008 | Suzuki et al. |
| 2009/0167168 A1* | 7/2009 | Seo et al. ................... 313/504 |

FOREIGN PATENT DOCUMENTS

| | | |
|---|---|---|
| CN | 1746163 A | 3/2006 |
| DE | 60108726 T2 | 7/2005 |
| EP | 1932842 A1 | 6/2008 |
| EP | 1993154 A1 | 11/2008 |
| JP | 2006-131799 A | 5/2006 |
| JP | 2007-001879 A | 1/2007 |
| JP | 2007-070282 A | 3/2007 |
| JP | 2008-120688 A | 5/2008 |
| JP | 2008-150365 A | 7/2008 |
| JP | 2008-208065 A | 9/2008 |
| JP | 2008-222624 A | 9/2008 |
| JP | 2008-235879 A | 10/2008 |
| JP | 2008-247895 A | 10/2008 |
| WO | 01/62869 A1 | 8/2001 |
| WO | 2004006355 A2 | 1/2004 |

OTHER PUBLICATIONS

Journal of Organic Chemistry, (2009), 74(8), pp. 3175-3178.*
Journal of the American Chemical Society, (2006), 128(34), pp. 10992-10993.*
First examination opinion notification issued by the China Intellectual Property Office on Jan. 31, 2012, for the above-referenced application's counterpart application in China (Application No. 201010258207.0).

* cited by examiner

*Primary Examiner* — Dawn L. Garrett
(74) *Attorney, Agent, or Firm* — Pai Patent & Trademark Law Firm; Chao-Chang David Pai

(57) ABSTRACT

A quinoxaline derivative represented by Formula (I) or (II) is provided. In Formula (I) or (II), $R_1$ and $R_2$ are, independently, hydrogen, halogen, methyl, ethyl, propyl, butyl, aryl or heteroaryl, for example phenyl, furyl, thienyl, pyridyl, pyrimidyl, benzothiazolyl or benzoimidazolyl. An organic light-emitting diode including the quinoxaline derivative is also provided.

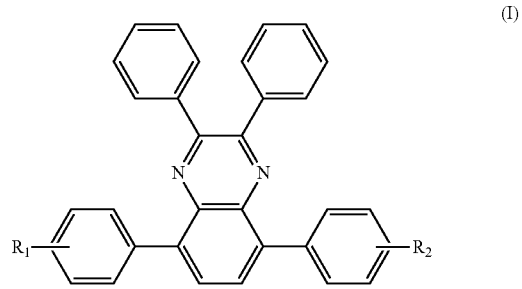

(I)

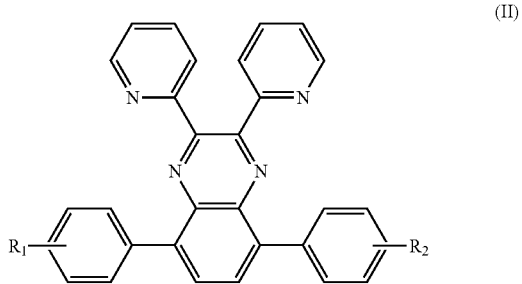

(II)

5 Claims, No Drawings

QUINOXALINE DERIVATIVES AND ORGANIC LIGHT-EMITTING DIODES COMPRISING THE SAME

CROSS REFERENCE TO RELATED APPLICATIONS

This Application claims priorities of Taiwan Patent Application No. 098129006, filed on Aug. 28, 2009 and No. 99124279, filed on Jul. 23, 2010, the entirety of which is incorporated by reference herein.

BACKGROUND OF THE INVENTION

1. Field of the Invention

The invention relates to a heterocyclic derivative, and more particularly to a quinoxaline derivative used in an organic light-emitting diode.

2. Description of the Related Art

Organic light-emitting diodes (OLED) are popularly applied in flat panel displays and flexible displays due to their light weight, thin profile, self-illuminating, low power consumption, no backlight requirement, wide viewing angle, rapid response time and capability to fabricate on flexible substrate. Meanwhile, conventional electron transport material has a carrier mobility which is 1% that of hole transport material and has low thermal stability, resulting in low luminescent efficiency and a short lifespan. Also, the charge consumption of electron transport materials is 35.96%, while that of a light-emitting layer is 39.8%. Thus, development of an electron transport material with high carrier mobility which may be used in OLEDs is desirable.

Accordingly, $Alq_3$, which has superior film-forming properties, have been developed and applied in electron transport materials and host materials. Additionally, metal (Be, Al, Zn) complexes, 1,2,4-triazoles (TAZ) derivatives, fluorine-containing compounds and silicon-containing compounds have also been developed and applied in electron transport materials due to their higher carrier mobility and Tg when compared to $Alq_3$. However, carrier mobility, thermal stability and current density of the materials are still insufficient for use in electron transport materials.

BRIEF SUMMARY OF THE INVENTION

One embodiment of the invention provides a quinoxaline derivative represented by Formula (I) or (II).

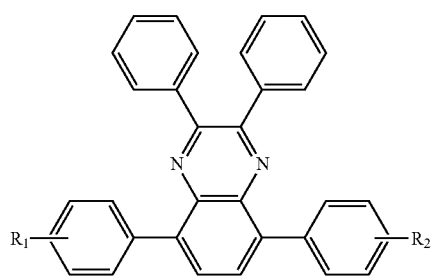

(I)

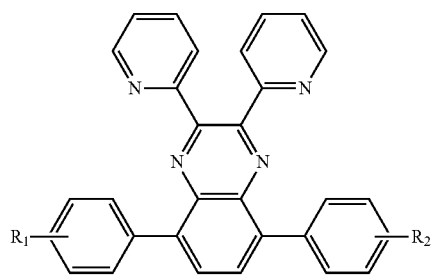

(II)

In Formula (I) or (II), $R_1$ and $R_2$ are, independently, hydrogen, halogen, methyl, ethyl, propyl, butyl, aryl or heteroaryl.

One embodiment of the invention provides an organic light-emitting diode comprising a cathode and an anode, a light-emitting layer disposed between the cathode and the anode, and an electron transport layer comprising the disclosed quinoxaline derivative represented by Formula (I) or (II) disposed between the light-emitting layer and the cathode.

A detailed description is given in the following embodiments.

DETAILED DESCRIPTION OF THE INVENTION

The following description is of the contemplated mode of carrying out the invention. This description is made for the purpose of illustrating the general principles of the invention and should not be taken in a limiting sense. The scope of the invention is best determined by reference to the appended claims.

One embodiment of the invention provides a quinoxaline derivative represented by Formula (I) or (II).

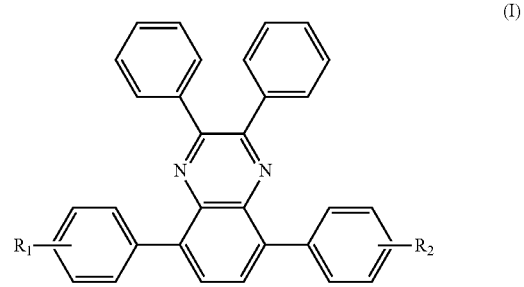

(I)

(II)

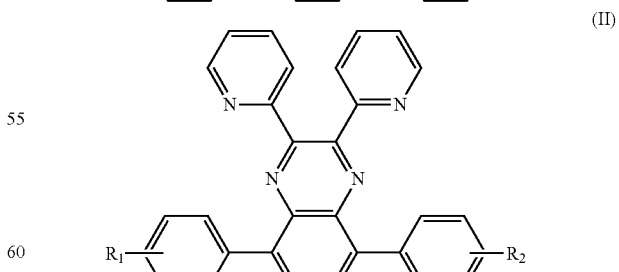

In Formula (I) or (II), $R_1$ and $R_2$ may be, independently, hydrogen, halogen, methyl, ethyl, propyl, butyl, aryl or heteroaryl, for example, phenyl, furyl, thienyl, pyridyl, pyrimidyl, benzothiazolyl or benzoimidazolyl.

Some specific quinoxaline derivatives provided by the invention are disclosed as follows.
C2
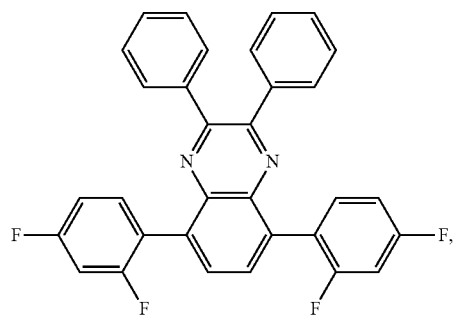
C3
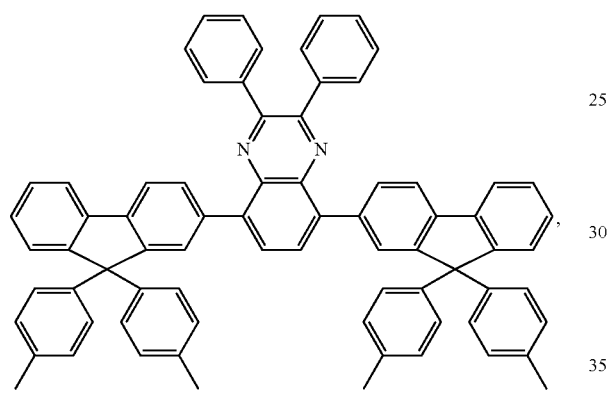
C4
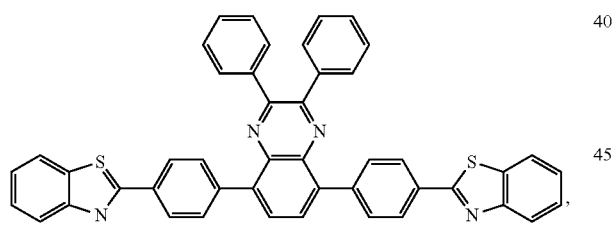
C5
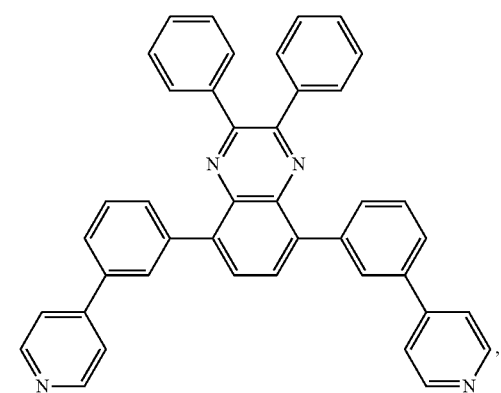
C6
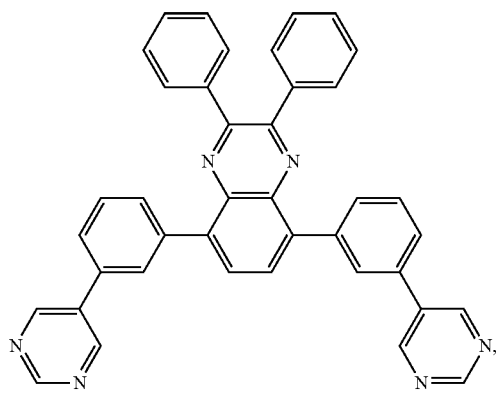
NE1
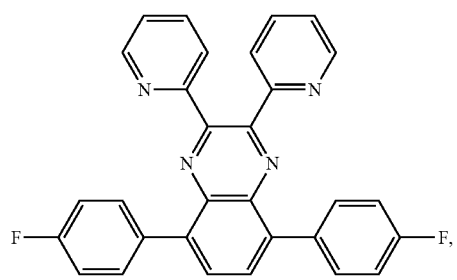
NE2
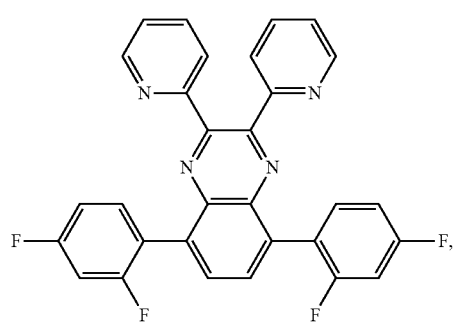
NE3
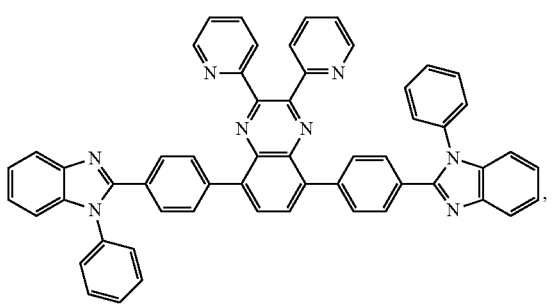

NE4

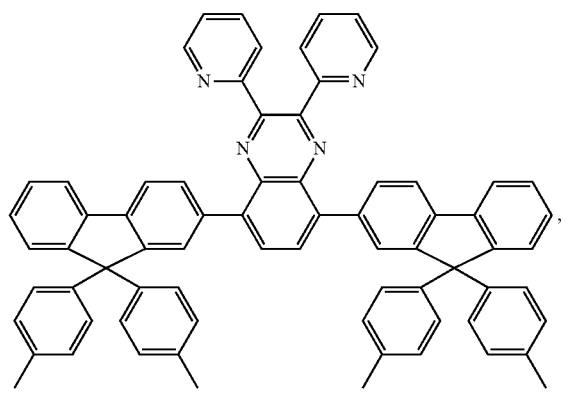

NE5

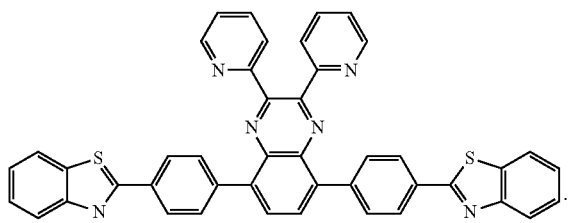

One embodiment of the invention provides an organic light-emitting diode comprising a cathode and an anode, a light-emitting layer disposed between the cathode and the anode, and an electron transport layer comprising the disclosed quinoxaline derivative represented by Formula (I) or (II) disposed between the light-emitting layer and the cathode.

The disclosed organic light-emitting diode may further comprise a hole transport layer, a hole blocking layer or a buffer layer. The hole transport layer may comprise HTM2, TPD, NPB, PPD, TBPB, spiro-TAD, spiro-NPB, TPTE2, TPTE1, NTPA or DNPD. The hole blocking layer may comprise Bphen, BCP, BAlq, CF-X, TAZ or CF-Y. The buffer layer may comprise LiF or $Li_2O$. The above-mentioned abbreviations represent the following structures.

TAZ

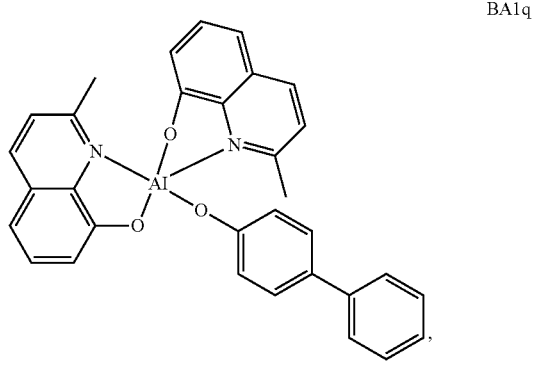

BAlq

HTM2

TPD

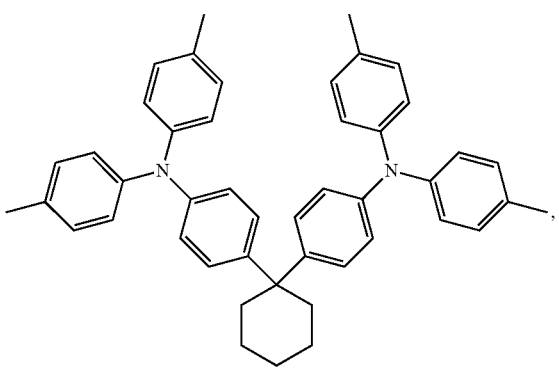

NPB

PPD

TBPB
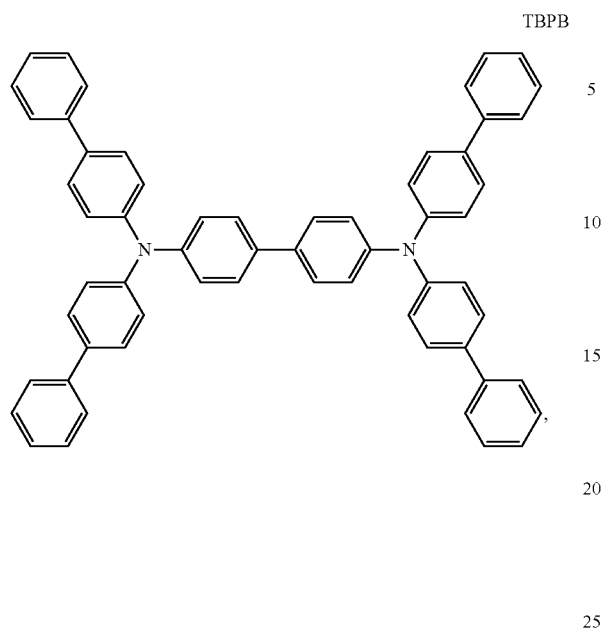
spiro-TAD
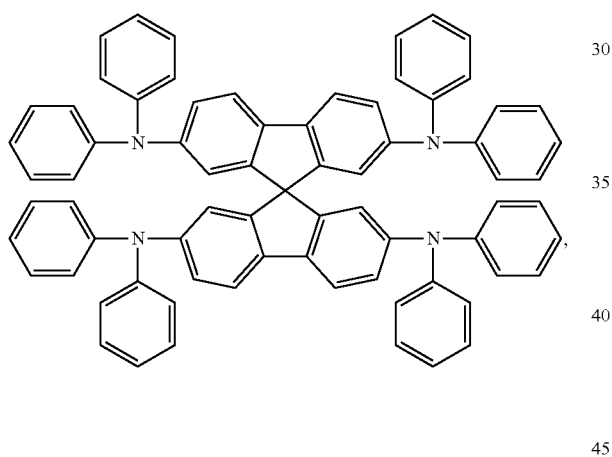
spiro-NPB
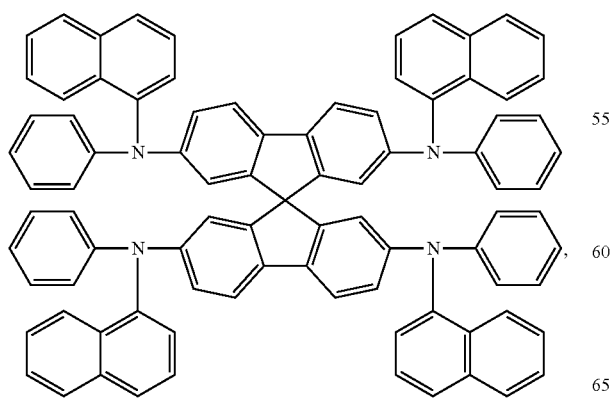
TPTE2
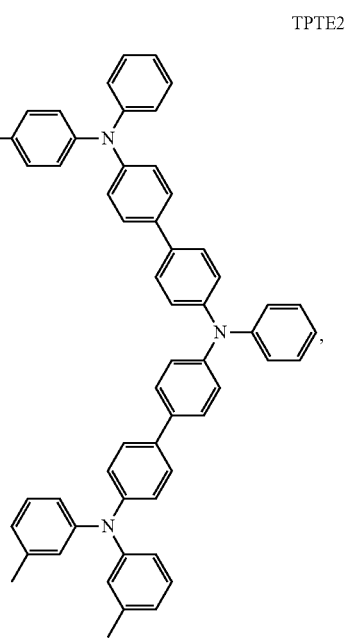
TPTE1
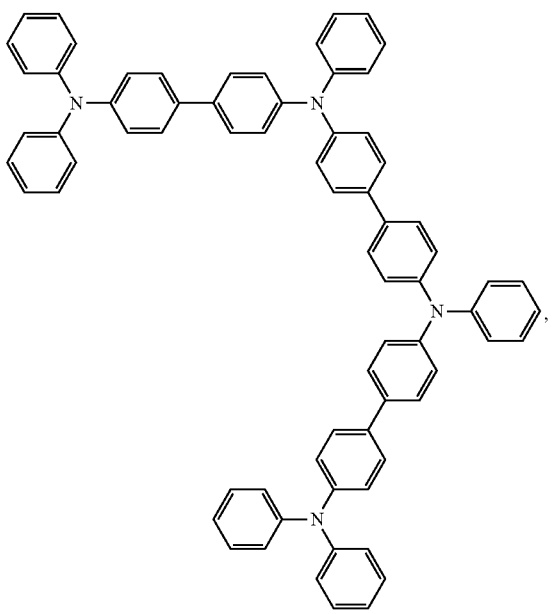

-continued

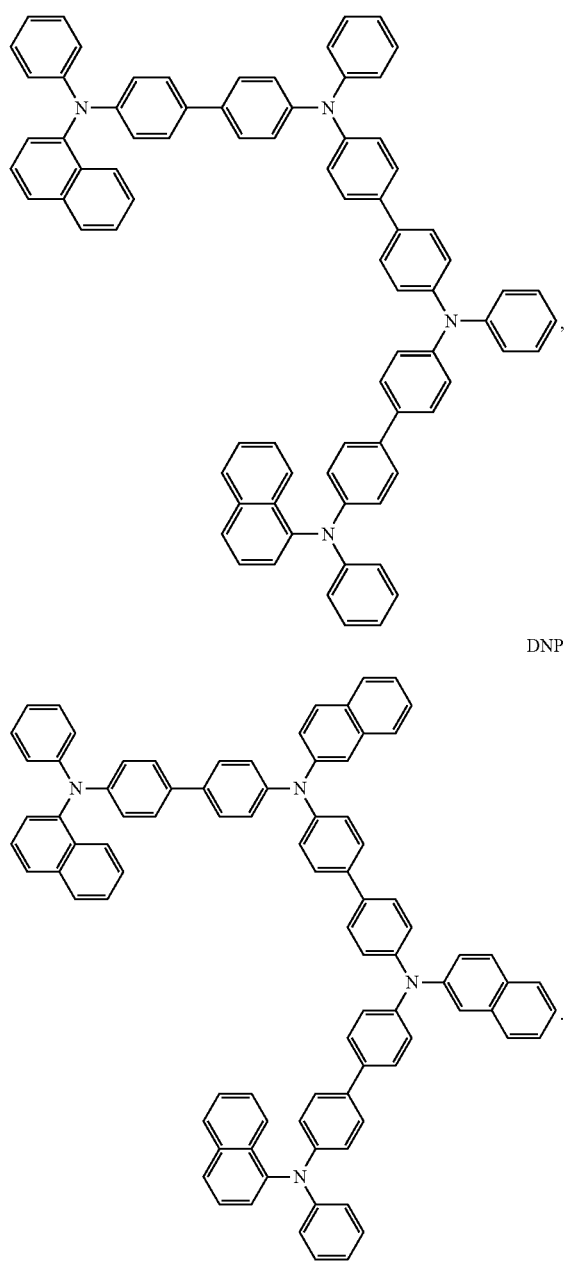

NTPA,

DNPD.

The invention provides an electron transport material with high electron transport rate used to fabricate phosphorescent OLEDs. The principal structure of the electron transport material is quinoxaline. The electron transport efficiency from the electron transport layer to the light-emitting layer is improved when compared to conventional methods due to the high electron transport rate. Thus, more efficient driving voltage and increased luminescent efficiency is achieved for blue and green phosphorescent OLEDs.

The disclosed electron transport material is composed of a nitrogen-containing quinoxaline heterocyclic compound with high electron transport rate. The electron transport material connected to, for example, a heterocyclic conjugate structure with high electron transport rate. Performance of PHOLED is improved by combination of such electron transport material and phosphorescent materials.

The LUMO energy level of the electron transport material is controlled by the quinoxaline heterocyclic compound connected to, for example, an aryl compound. The HOMO energy level of the electron transport material is further controlled by the substituted groups on the aryl compound. Reduced driving voltage and increased luminescent efficiency of PHOLED is achieved by combination of such electron transport material and phosphorescent materials.

EXAMPLE 1

Preparation of Compound C2

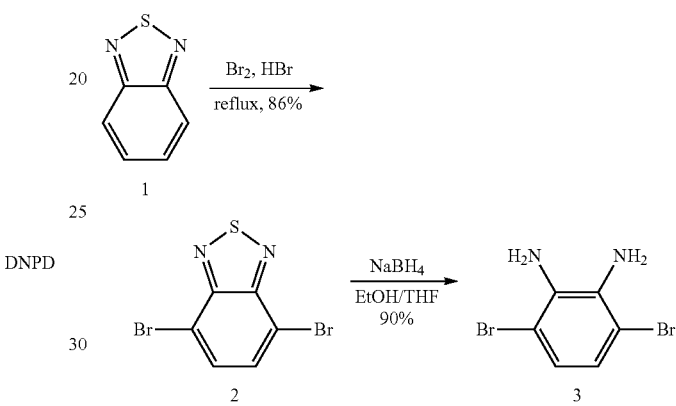

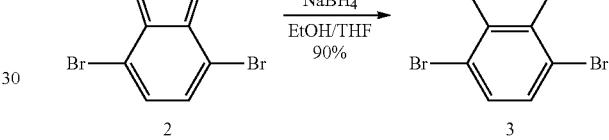

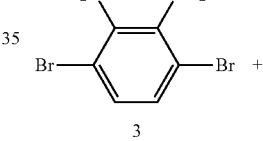

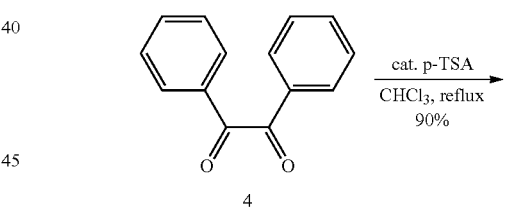

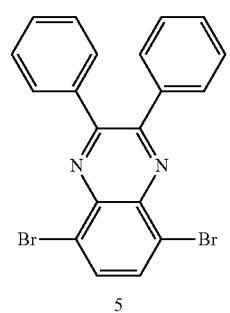

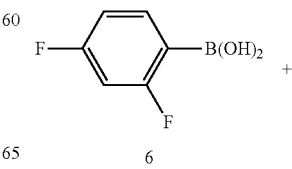

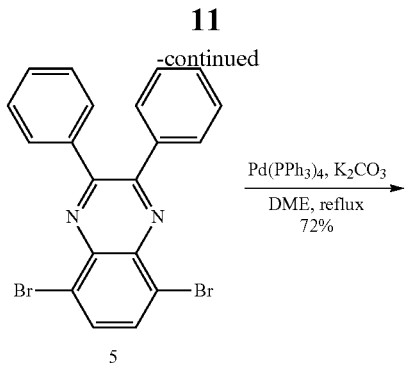

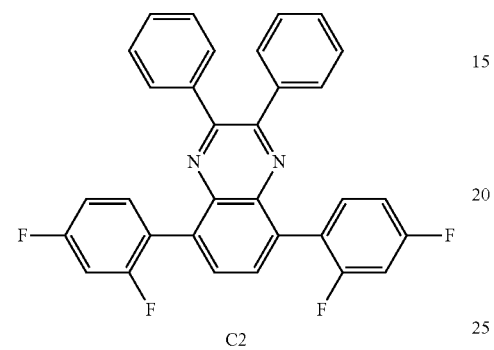

13.6 g of benzothiadiazole (100 mmol) (compound 1) and 300 mL of HBr aqueous solution (48%) were added to a 1,000 mL round-bottom flask and heated to reflux. 15.4 mL of bromine (300 mmol) was then slowly dropped and reacted overnight. After adding sodium thiosulfate aqueous solution to quench the reaction, the resulting solution was filtered. The filtered solid was then washed with acetone. Thus, 25.3 g of light ashen solid product (compound 2) was obtained, with a yield of 86%.

2.94 g of compound 2 (10 mmol), 150 mL of ethanol and 50 mL of THF were added to a 250 mL round-bottom flask and stirred for 10 minutes. 1.51 g of Sodium borohydride (10 mmol) was then added and heated to reflux. After reacting overnight, the resulting solution was filtered with a filter paper and extracted using ether and saturated saline. The organic layer was then collected. After removal of water of the collected solution by adding dry magnesium sulfate and concentrated by reducing the pressure, 2.4 g of white solid product (compound 3) was obtained, with a yield of 90%.

585 mg of compound 3 (2.2 mmol), 420 mg of benzil (2 mmol) (compound 4), a specific amount of p-toluenesulfonic acid monohydrate (p-TSA) and 20 mL of trichloromethane were added to a 50 mL two-necked flask and heated to reflux. After reacting for 12 hours, 20 mL of sodium bicarbonate aqueous solution was added to quench the reaction. The resulting solution was then extracted using 20 mL of dichloromethane for several times. The organic layer was then washed with saturated saline and collected. After removal of water of the collected solution by adding dry magnesium sulfate, filtered and concentrated by reducing the pressure, the concentrated results were purified using column chromatography (silicon dioxide, n-hexane/ethyl acetate=19/1). Thus, 820 mg of light yellow solid product (compound 5) was obtained, with a yield of 90%.

695 mg of compound 6 (4.4 mmol), 910 mg of compound 5 (2 mmol), 115.5 mg of Pd(PPh$_3$)$_4$ (0.1 mmol), 2.1 mL of K$_2$CO$_3$ (2M in H$_2$O, 4.2 mmol) and 50 mL of dimethoxyethane (DME) were added to a 150 mL two-necked flask and heated to reflux for 24 hours. The resulting solution was then extracted using 20 mL of ethyl acetate for several times. The organic layer was then washed with saturated saline and collected. After removal of water of the collected solution by adding dry magnesium sulfate, filtered and concentrated by reducing the pressure, the concentrated results were purified using column chromatography (silicon dioxide, trichloromethane/n-hexane=1/4). Thus, 750 mg of light yellow solid product (compound C2) was obtained, with a yield of 72%.

$^1$H NMR (CDCl$_3$, 200 MHz) δ7.79 (s, 2H), 7.54-7.61 (m, 2H), 7.47 (dd, J=8.0, 2.2 Hz, 4H), 7.18-7.33 (m, 6H), 6.93-7.04 (m, 4H).

Compound C2 possessed a carrier mobility of 6×10$^{-5}$ cm$^2$/Vs, apparently superior to that of conventional Alq3 of 2×10$^{-6}$ cm$^2$/Vs.

EXAMPLE 2

Preparation of Compound C3

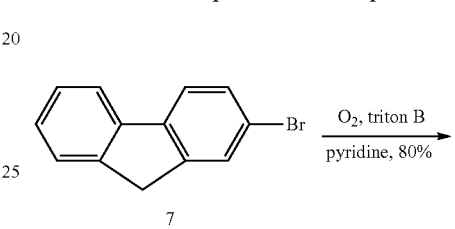

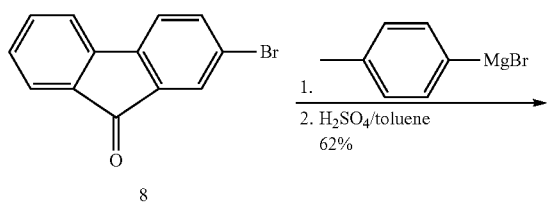

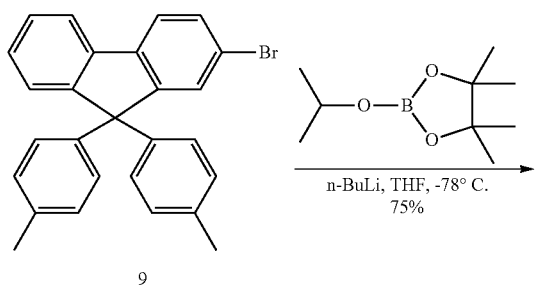

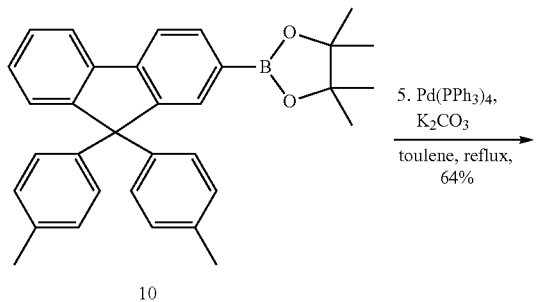

-continued

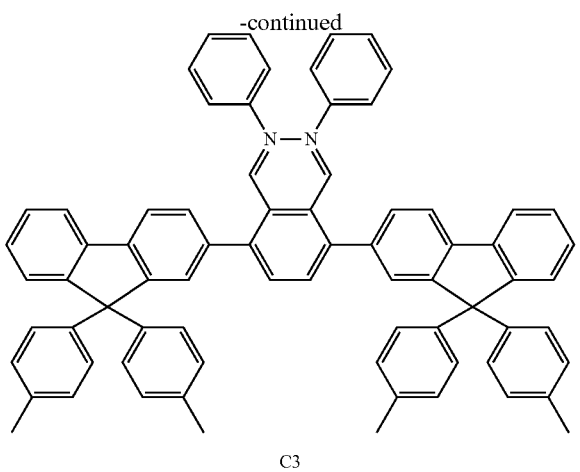

C3

25 g of 2-bromo-fluorene (2 mmol) (compound 7), 300 mL of pyridine and 5 mL of benzyltrimethyl ammonium hydroxide (triton B) were added to a 500 mL conical flask. Next, a high-pressured oxygen gas was conducted. After reacting for 6 hours, 200 mL of acetic acid was added to quench the reaction. After the resulting solution was filtered, 21.7 g of golden yellow solid product (compound 8) was obtained, with a yield of 80%.

1.215 g of a piece of magnesium (50 mmol) was added to a 500 mL of two-necked flask connected with a condensing tube and a feeding tube. After removal of water by baking under vacuum, a piece of iodine was added. 50 mL of dry THF and 6.15 mL of 4-bromo toluene (100 mmol) were then slowly dropped from the feeding tube and then heated to reflux. After magnesium is completely reacted, 6.4 g of compound 8 (25.0 mmol) dissolved in 150 mL of THF was slowly dropped form the feeding tube under reflux. After dropping is completed, reflux continuously proceeded for 4 hours. Water was then added to quench the reaction. After the resulting solution was extracted with ether and concentrated, a brown liquid intermediate was obtained. 200 mL of toluene and 3 mL of conc. H$_2$SO$_4$ were added to a 1,000 mL two-necked flask connected with a feeding tube and heated to 60° C. The intermediate dissolved in 100 mL of toluene was then slowly dropped into the 1,000 mL two-necked flask through the feeding tube. After dropping is completed, dry potassium carbonate solid was added. The resulting solution was then filtered and concentrated. The concentrated results were then purified using a silica gel column (eluent: hexane). Thus, 6.51 g of white product (compound 9) was obtained, with a yield of 62%.

3.0 g of compound 9 (7.1 mmol) and 100 mL of dry THF were added to a 250 mL two-necked flask and cooled to −78° C. 2.2 mL of n-butyl lithium (1.6M, 10.6 mmole) was then added to react for 5 hours. 6.6 mL of 2-isopropoxy-4,4,5,5-tetramethyl-1,3,2-dioxaborolane (10.6 mmol) was then added at the same temperature of −78° C. After returning to room temperature and then reacting for 8 hours, n-hexane was added to quench the reaction. The resulting solution was then extracted using 20 mL of ethyl acetate for several times. The organic layer was then washed with saturated saline and collected. After removal of water of the collected solution by adding dry magnesium sulfate, filtered and concentrated by reducing the pressure, the concentrated results were re-crystallized using methanol. Thus, 2.5 g of white solid product (compound 10) was obtained, with a yield of 75%.

2.5 g of compound 10 (5.3 mmol), 1.1 g of compound 5 (2.4 mmol), 139 mg of Pd(PPh$_3$)$_4$ (0.12 mmol), 2.5 mL of K$_2$CO$_3$ (2M in H$_2$O) and 100 mL of toluene were added to a 150 mL two-necked flask and heated to reflux for 18 hours. The resulting solution was then extracted using 20 mL of ethyl acetate for several times. The organic layer was then washed with saturated saline and collected. After removal of water of the collected solution by adding dry magnesium sulfate, filtered and concentrated by reducing the pressure, the concentrated results were purified using column chromatography (silicon dioxide, dichloromethane/n-hexane=1/4). Thus, 1.5 g of white solid product (compound C3) was obtained, with a yield of 64%.

$^1$H NMR (CDCl$_3$, 200 MHz) δ7.78-7.89 (m, 10H), 7.28-7.46 (m, 16H), 7.13 (d, J=7.0 Hz, 8H), 6.98 (d, J=8.0 Hz, 8H), 2.27 (s, 12H).

EXAMPLE 3

Preparation of Compound C4

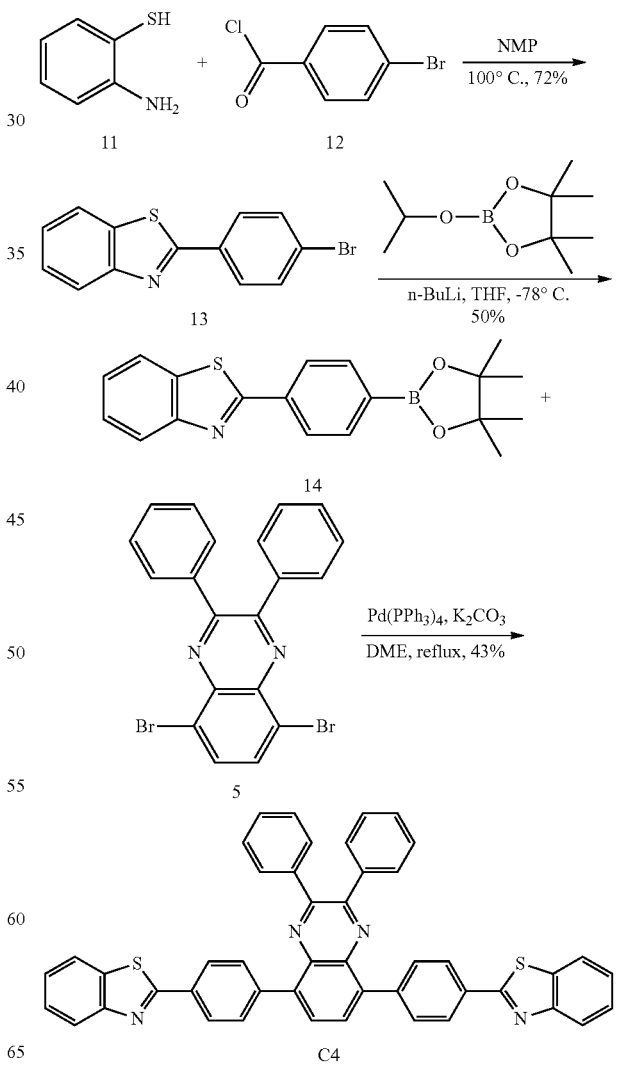

4.4 g of compound 12 (20 mmol), 50 mL of N-methyl-pyrrolidinone (NMP) and 2.1 mL of compound 11 (20 mmol) were added to a 250 mL two-necked flask and heated to 100° C. After one hour, the temperature was lowered to room temperature. Aqueous ammonia was then added to alkalize the resulting solution to the pH 8-9. After filtering and washing the filtered results with water, 4.1 g of white solid product (compound 13) was obtained, with a yield of 72%.

3.3 g of compound 13 (11.4 mmol) and 100 mL of dry THF were added to a 250 mL two-necked flask and cooled to −78° C. 10.7 mL of n-butyl lithium (1.6M, 17.1 mmole) was then added to react for 0.5 hour. 3.5 mL of 2-isopropoxy-4,4,5,5-tetramethyl-1,3,2-dioxaborolane (17.1 mmol) was then added at the same temperature of −78° C. After returning to room temperature and then reacting for 12 hours, the resulting solution was extracted using ethyl acetate and saturated saline. The organic layer was then collected. After removal of water of the collected solution by adding dry magnesium sulfate, filtered and concentrated by reducing the pressure, the concentrated results were re-crystallized using methanol. Thus, 1.9 g of white solid product (compound 14) was obtained, with a yield of 50%.

1.8 g of compound 14 (5.3 mmol), 1.1 g of compound 5 (2.4 mmol), 280 mg of Pd(PPh$_3$)$_4$ (0.24 mmol), 2.4 mL of K$_2$CO$_3$ (2M in H$_2$O) and 100 mL of DME were added to a 250 mL two-necked flask and heated to reflux for 48 hours. The resulting solution was then extracted using 20 mL of dichloromethane for several times. The organic layer was then washed with saturated saline and collected. After removal of water of the collected solution by adding dry magnesium sulfate, filtered and concentrated by reducing the pressure, the concentrated results were purified using column chromatography (silicon dioxide, dichloromethane/n-hexane=1/4). Thus, 1.6 g of yellow solid product (compound C4) was obtained, with a yield of 63%.

$^1$H NMR (CDCl$_3$, 200 MHz) δ8.23 (d, J=8.0 Hz, 2H), 8.18 (d, J=7.6 Hz, 2H), 7.80-8.00 (m, 6H), 7.47-7.61 (m, 6H), 7.27-7.44 (m, 10H).

EXAMPLE 4

Preparation of Compound C5

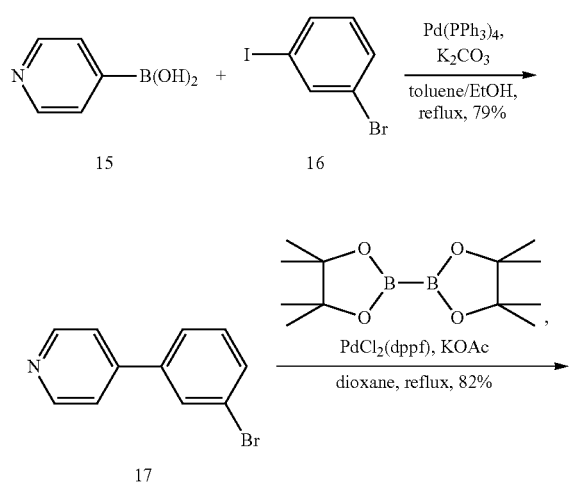

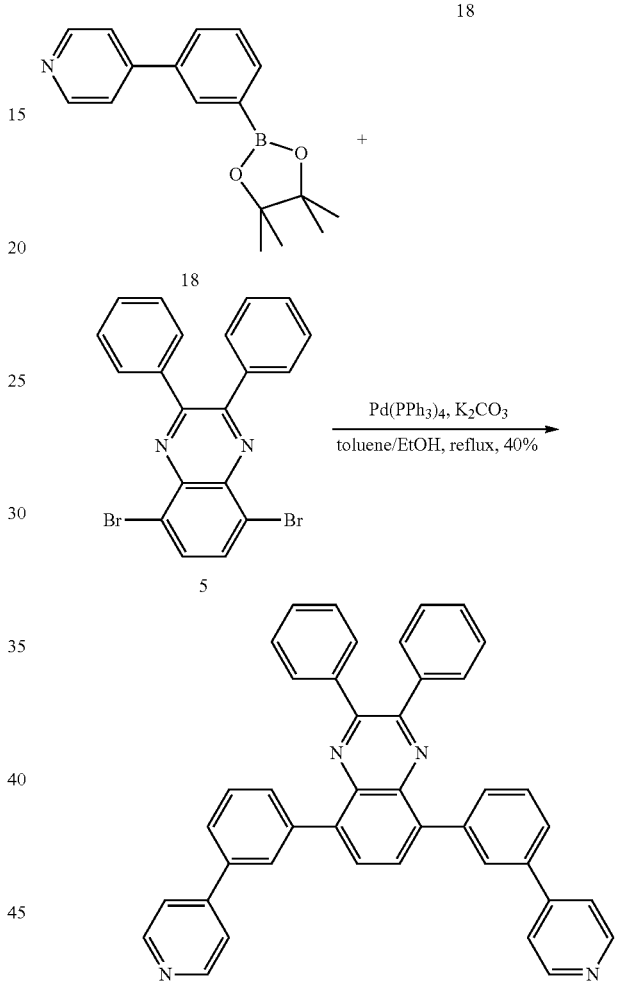

5.0 g of compound 15 (40.6 mmol), 11.5 g of compound 16 (40.6 mmol), 2.3 g of Pd(PPh$_3$)$_4$ (2.0 mmol), 43 mL of K$_2$CO$_3$ (2M), 100 mL of toluene and 50 mL of ethanol were added to a 500 mL two-necked flask and heated to reflux for 24 hours under nitrogen gas. After returning to room temperature, the resulting solution was extracted using 20 mL of dichloromethane for several times. The organic layer was then washed with saturated saline and collected. After removal of water of the collected solution by adding dry magnesium sulfate, filtered and concentrated by reducing the pressure, the concentrated results were purified using column chromatography (silicon dioxide, trichloromethane/ethyl acetate=3/1). Thus, 7.5 g of colorless liquid product (compound 17) was obtained, with a yield of 79%.

1.0 g of compound 17 (4.27 mmol), 1.2 g of bis(pinacolato)diboron (4.7 mmol), 174 mg of PdCl$_2$(dppf) (0.21 mmol), 1.3 g of potassium acetate (12.8 mmol) and 50 mL of dry dioxane were added to a 250 mL two-necked flask and heated to 80° C. with stirring for 24 hours. After the temperature was lowered to room temperature, the resulting solution was filtered with Celite545 and extracted using ethyl acetate and saturated saline. After removal of water of the extracted solution by adding dry magnesium sulfate, filtered and concentrated by reducing the pressure, the concentrated results were purified using column chromatography (silicon dioxide, trichloromethane/ethyl acetate=2/1). Thus, 984 mg of light yellow solid product (compound 18) was obtained, with a yield of 82%.

1.49 g of compound 18 (5.3 mmol), 1.1 g of compound 5 (2.4 mmol), 280 mg of Pd(PPh$_3$)$_4$ (0.24 mmol), 2.4 mL of K$_2$CO$_3$ (2M in H$_2$O), 100 mL of toluene and 50 mL of ethanol were added to a 250 mL two-necked flask and heated to reflux for 48 hours. The resulting solution was then extracted using 30 mL of trichloromethane for several times. The organic layer was then washed with saturated saline and collected. After removal of water of the collected solution by adding dry magnesium sulfate, filtered and concentrated by reducing the pressure, the concentrated results were purified using column chromatography (silicon dioxide, trichloromethane/ethyl acetate=2/1). Thus, 1.25 g of gray solid product (compound C5) was obtained, with a yield of 40%.

EXAMPLE 5

Preparation of Compound C6

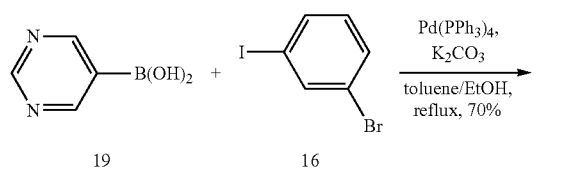

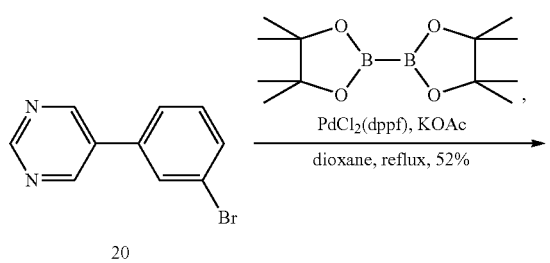

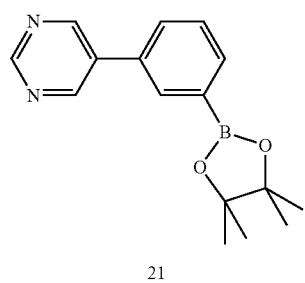

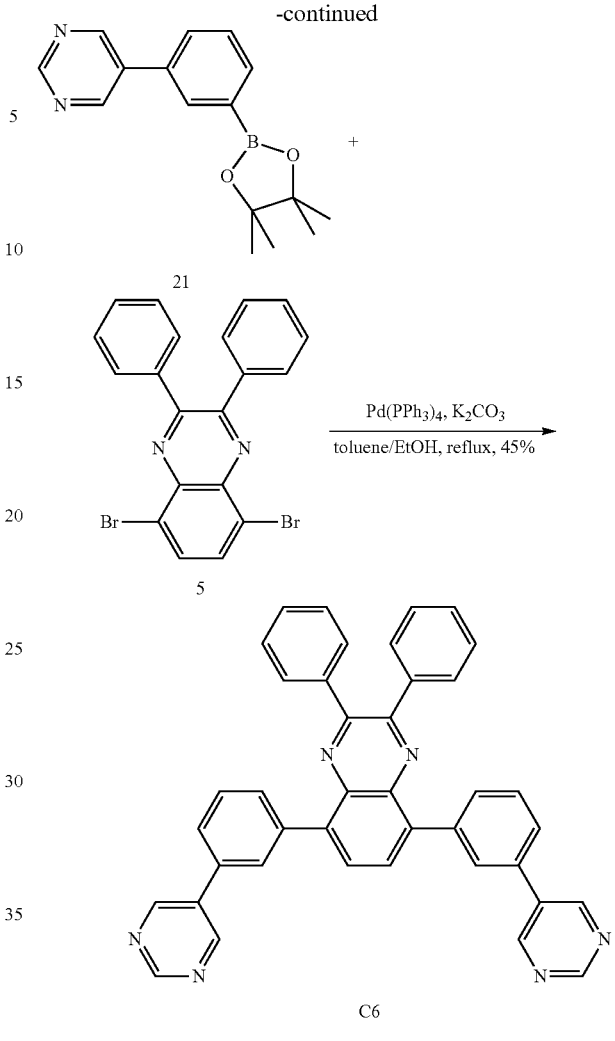

2.0 g of compound 19 (16.1 mmol), 4.6 g of compound 16 (16.1 mmol), 930 mg of Pd(PPh$_3$)$_4$ (0.81 mmol), 4.3 mL of K$_2$CO$_3$ (2M in H$_2$O), 100 mL of toluene and 50 mL ethanol were added to a 500 mL two-necked flask and heated to reflux for 24 hours under nitrogen gas. After returning to room temperature, the resulting solution was extracted using 20 mL of dichloromethane for several times. The organic layer was then washed with saturated saline and collected. After removal of water of the collected solution by adding dry magnesium sulfate, filtered and concentrated by reducing the pressure, the concentrated results were purified using column chromatography (silicon dioxide, trichloromethane/ethyl acetate=3/1). Thus, 7.5 g of colorless liquid product (compound 20) was obtained, with a yield of 70%.

1.0 g of compound 20 (4.27 mmol), 1.2 g of bis(pinacolato) diboron (4.7 mmol), 174 mg of PdCl$_2$(dppf) (0.21 mmol), 1.3 g of potassium acetate (12.8 mmol) and 50 mL of dry dioxane were added to a 250 mL two-necked flask and heated to 80° C. with stirring for 24 hours. After the temperature was lowered to room temperature, the resulting solution was filtered with Celite545 and extracted using ethyl acetate and saturated saline. After removal of water of the extracted solution by adding dry magnesium sulfate, filtered and concentrated by reducing the pressure, the concentrated results were purified using column chromatography (silicon dioxide, trichloromethane/ethyl acetate=2/1). Thus, 626 mg of light yellow solid product (compound 21) was obtained, with a yield of 52%.

1.49 g of compound 21 (5.3 mmol), 1.1 g of compound 5 (2.4 mmol), 280 mg of Pd(PPh$_3$)$_4$ (0.24 mmol), 2.4 mL of K$_2$CO$_3$ (2M in H$_2$O), 100 mL of toluene and 50 mL of ethanol were added to a 250 mL two-necked flask and heated to reflux for 48 hours. The resulting solution was then extracted using 30 mL of trichloromethane for several times. The organic layer was then washed with saturated saline and collected. After removal of water of the collected solution by adding dry magnesium sulfate, filtered and concentrated by reducing the pressure, the concentrated results were purified using column chromatography (silicon dioxide, trichloromethane/ethyl acetate=2/1). Thus, 1.41 g of gray solid product (compound C6) was obtained, with a yield of 45%.

EXAMPLE 6

Preparation of Compound NE1

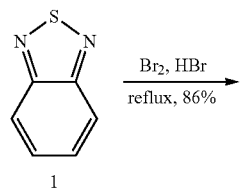

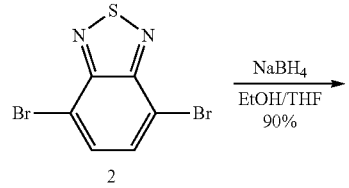

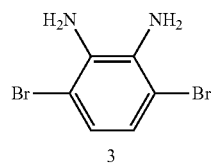

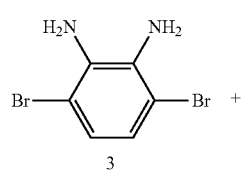

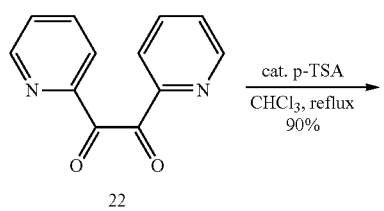

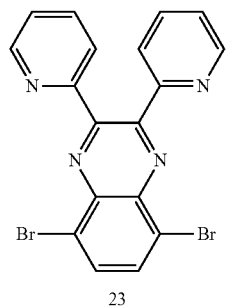

23
Chemical Formula: C$_{18}$H$_{10}$Br$_2$N$_4$
Molecular Weight: 442.11

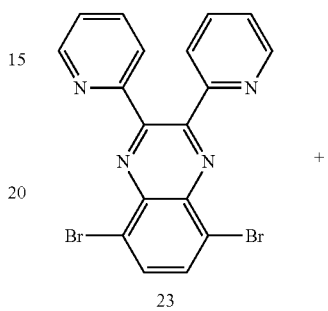

6
Chemical Formula: C$_{12}$H$_{16}$BFO$_2$
Molecular Weight: 222.06

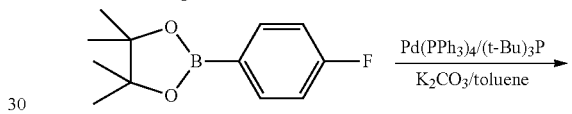

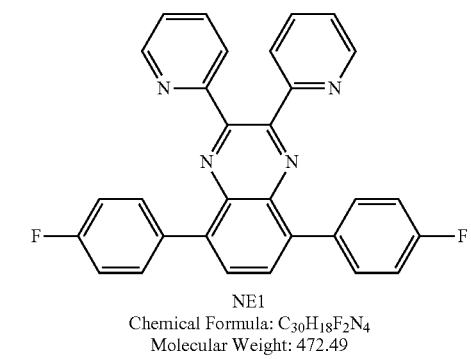

NE1
Chemical Formula: C$_{30}$H$_{18}$F$_2$N$_4$
Molecular Weight: 472.49

13.6 g of benzothiadiazole (100 mmol) (compound 1) and 300 mL of HBr aqueous solution (48%) were added to a 1,000 mL round-bottom flask and heated to reflux. 15.4 mL of bromine (300 mmol) was then slowly dropped and reacted overnight. After adding sodium thiosulfate aqueous solution to quench the reaction, the resulting solution was filtered. The filtered solid was then washed with acetone. Thus, 25.3 g of light ashen solid product (compound 2) was obtained, with a yield of 86%.

2.94 g of compound 2 (10 mmol), 150 mL of ethanol and 50 mL of THF were added to a 250 mL round-bottom flask and stirred for 10 minutes. 1.51 g of Sodium borohydride (10 mmol) was then added and heated to reflux. After reacting overnight, the resulting solution was filtered with a filter paper and extracted using ether and saturated saline. The organic layer was then collected. After removal of water of the collected solution by adding dry magnesium sulfate and concentrated by reducing the pressure, 2.4 g of white solid product (compound 3) was obtained, with a yield of 90%.

585 mg of compound 3 (2.2 mmol), 420 mg of compound 22 (2 mmol), a specific amount of p-toluenesulfonic acid monohydrate (p-TSA) and 20 mL of trichloromethane were added to a 50 mL two-necked flask and heated to reflux. After reacting for 12 hours, 20 mL of sodium bicarbonate aqueous solution was added to quench the reaction. The resulting solution was then extracted using 20 mL of dichloromethane for several times. The organic layer was then washed with saturated saline and collected. After removal of water of the collected solution by adding dry magnesium sulfate, filtered and concentrated by reducing the pressure, the concentrated results were re-precipitated by dropping methanol. Thus, 875 mg of light yellow solid product (compound 23) was obtained, with a yield of 90%.

1.39 g of compound 6 (9.9 mol), 2 g of compound 23 (4.5 mmol), 313 mg of Pd(PPh$_3$)$_4$ (0.27 mmol), 165 mg of P(t-Bu)$_3$ (0.81 mmol), 5.8 mL of K$_2$CO$_3$ (2M in H$_2$O, 11.7 mmol) and 80 mL of toluene were added to a 150 mL two-necked flask and heated to reflux for 24 hours. The resulting solution was then extracted using dichloromethane for several times. The organic layer was then washed with saturated saline and collected. After removal of water of the collected solution by adding dry magnesium sulfate, filtered and concentrated by reducing the pressure, the concentrated results were re-precipitated by dropping an equivalent amount of methanol. Thus, 1.73 g of white solid product (compound NE1) was obtained, with a yield of 81%.

EXAMPLE 7

Preparation of Compound NE2

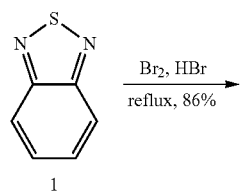

1

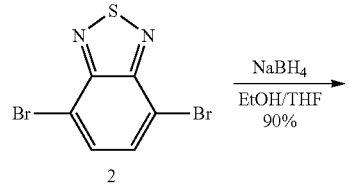

2

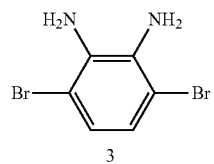

3

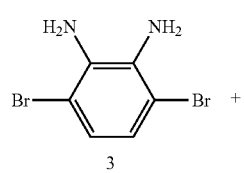

3

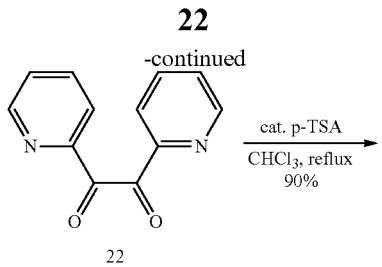

22

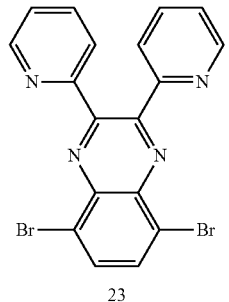

23

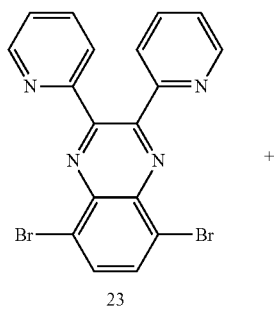

23
Chemical Formula: C$_{18}$H$_{10}$Br$_2$N$_4$
Molecular Weight: 442.11

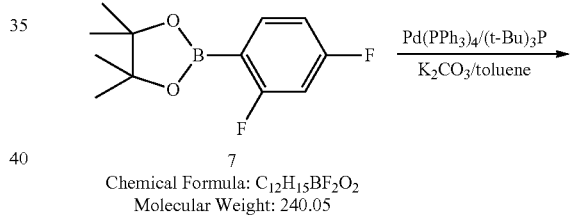

7
Chemical Formula: C$_{12}$H$_{15}$BF$_2$O$_2$
Molecular Weight: 240.05

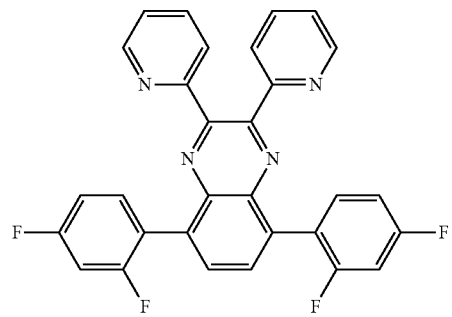

NE2
Chemical Formula: C$_{30}$H$_{16}$F$_4$N$_4$
Molecular Weight: 508.47

13.6 g of benzothiadiazole (100 mmol) (compound 1) and 300 mL of HBr aqueous solution (48%) were added to a 1,000 mL round-bottom flask and heated to reflux. 15.4 mL of bromine (300 mmol) was then slowly dropped and reacted overnight. After adding sodium thiosulfate aqueous solution to quench the reaction, the resulting solution was filtered. The filtered solid was then washed with acetone. Thus, 25.3 g of light ashen solid product (compound 2) was obtained, with a yield of 86%.

2.94 g of compound 2 (10 mmol), 150 mL of ethanol and 50 mL of THF were added to a 250 mL round-bottom flask and stirred for 10 minutes. 1.51 g of Sodium borohydride (10 mmol) was then added and heated to reflux. After reacting overnight, the resulting solution was filtered with a filter paper and extracted using ether and saturated saline. The organic layer was then collected. After removal of water of the collected solution by adding dry magnesium sulfate and concentrated by reducing the pressure, 2.4 g of white solid product (compound 3) was obtained, with a yield of 90%.

585 mg of compound 3 (2.2 mmol), 420 mg of compound 22 (2 mmol), a specific amount of p-toluenesulfonic acid monohydrate (p-TSA) and 20 mL of trichloromethane were added to a 50 mL two-necked flask and heated to reflux. After reacting for 12 hours, 20 mL of sodium bicarbonate aqueous solution was added to quench the reaction. The resulting solution was then extracted using 20 mL of dichloromethane for several times. The organic layer was then washed with saturated saline and collected. After removal of water of the collected solution by adding dry magnesium sulfate, filtered and concentrated by reducing the pressure, the concentrated results were re-precipitated by dropping methanol. Thus, 875 mg of light yellow solid product (compound 23) was obtained, with a yield of 90%.

2.3 g of compound 7 (9.5 mol), 2 g of compound 23 (4.5 mmol), 313 mg of Pd(PPh$_3$)$_4$ (0.27 mmol), 165 mg of P(t-Bu)$_3$ (0.81 mmol), 5.8 mL of K$_2$CO$_3$ (2M in H$_2$O, 11.7 mmol) and 80 mL of toluene were added to a 150 mL two-necked flask and heated to reflux for 24 hours. The resulting solution was then extracted using dichloromethane for several times. The organic layer was then washed with saturated saline and collected. After removal of water of the collected solution by adding dry magnesium sulfate, filtered and concentrated by reducing the pressure, the concentrated results were re-precipitated by dropping an equivalent amount of methanol. Thus, 1.95 g of white solid product (compound NE2) was obtained, with a yield of 85%.

EXAMPLE 8

Preparation of Compound NE3

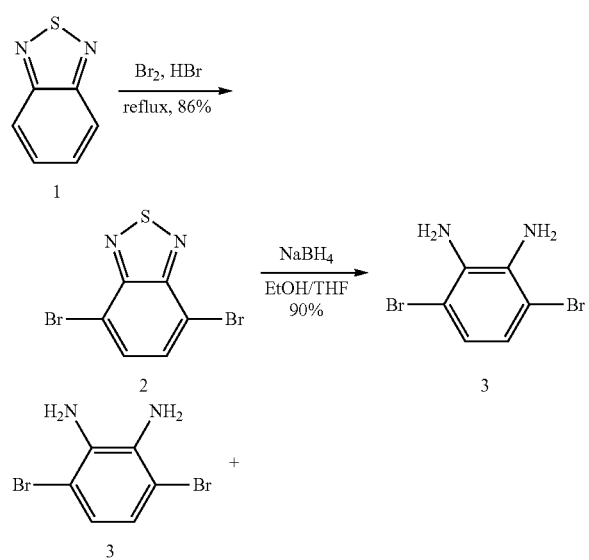

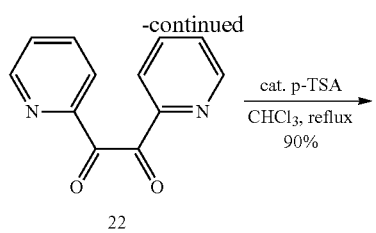

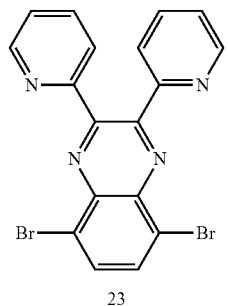

23
Chemical Formula: C$_{18}$H$_{10}$Br$_2$N$_4$
Molecular Weight: 442.11

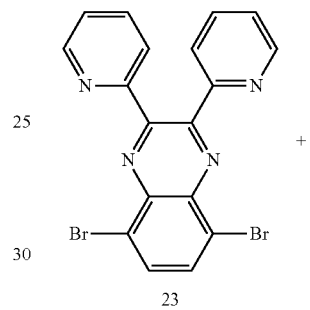

8
Chemical Formula: C$_{25}$H$_{25}$Bn$_2$O$_2$
Molecular Weight: 396.29

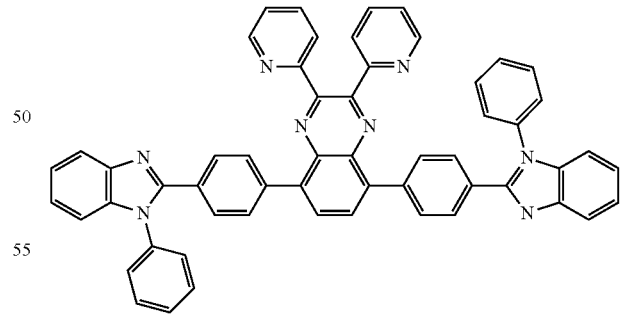

NE3
Chemical Formula: C$_{56}$H$_{36}$N$_8$
Molecular Weight: 820.94

13.6 g of benzothiadiazole (100 mmol) (compound 1) and 300 mL of HBr aqueous solution (48%) were added to a 1,000 mL round-bottom flask and heated to reflux. 15.4 mL of bromine (300 mmol) was then slowly dropped and reacted overnight. After adding sodium thiosulfate aqueous solution to quench the reaction, the resulting solution was filtered. The filtered solid was then washed with acetone. Thus, 25.3 g of light ashen solid product (compound 2) was obtained, with a yield of 86%.

2.94 g of compound 2 (10 mmol), 150 mL of ethanol and 50 mL of THF were added to a 250 mL round-bottom flask and stirred for 10 minutes. 1.51 g of Sodium borohydride (10 mmol) was then added and heated to reflux. After reacting overnight, the resulting solution was filtered with a filter paper and extracted using ether and saturated saline. The organic layer was then collected. After removal of water of the collected solution by adding dry magnesium sulfate and concentrated by reducing the pressure, 2.4 g of white solid product (compound 3) was obtained, with a yield of 90%.

585 mg of compound 3 (2.2 mmol), 420 mg of compound 22 (2 mmol), a specific amount of p-toluenesulfonic acid monohydrate (p-TSA) and 20 mL of trichloromethane were added to a 50 mL two-necked flask and heated to reflux. After reacting for 12 hours, 20 mL of sodium bicarbonate aqueous solution was added to quench the reaction. The resulting solution was then extracted using 20 mL of dichloromethane for several times. The organic layer was then washed with saturated saline and collected. After removal of water of the collected solution by adding dry magnesium sulfate, filtered and concentrated by reducing the pressure, the concentrated results were re-precipitated by dropping methanol. Thus, 875 mg of light yellow solid product (compound 23) was obtained, with a yield of 90%.

2.3 g of compound 8 (9.5 mol), 2 g of compound 23 (4.5 mmol), 313 mg of Pd(PPh$_3$)$_4$ (0.27 mmol), 165 mg of P(t-Bu)$_3$ (0.81 mmol), 5.8 mL of K$_2$CO$_3$ (2M in H$_2$O, 11.7 mmol) and 80 mL of toluene were added to a 150 mL two-necked flask and heated to reflux for 24 hours. The resulting solution was then extracted using dichloromethane for several times. The organic layer was then washed with saturated saline and collected. After removal of water of the collected solution by adding dry magnesium sulfate, filtered and concentrated by reducing the pressure, the concentrated results were re-precipitated by dropping an equivalent amount of methanol. Thus, 2.15 g of white solid product (compound NE3) was obtained, with a yield of 58%.

EXAMPLE 9

Preparation of Compound NE4

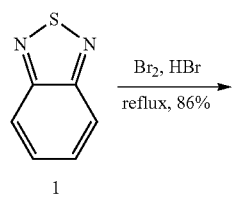

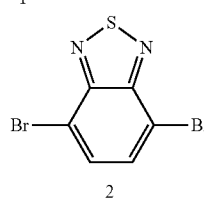

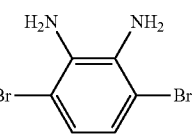

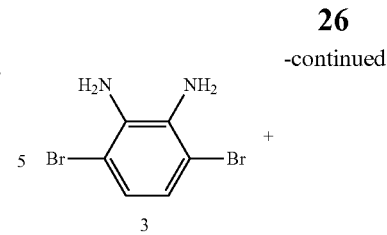

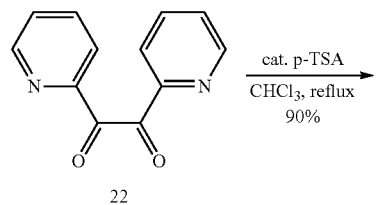

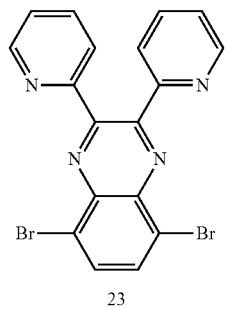

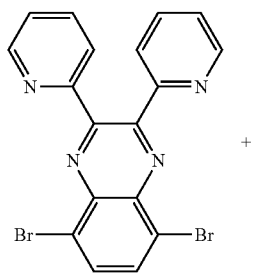

23
Chemical Formula: C$_{18}$H$_{10}$Br$_2$N$_4$
Molecular Weight: 442.11

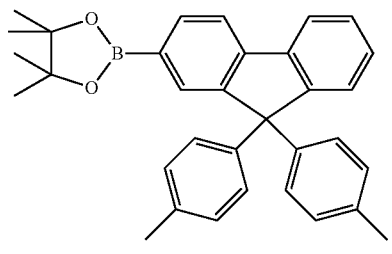

9
Chemical Formula: C$_{33}$H$_{33}$BO$_2$
Molecular Weight: 472.42

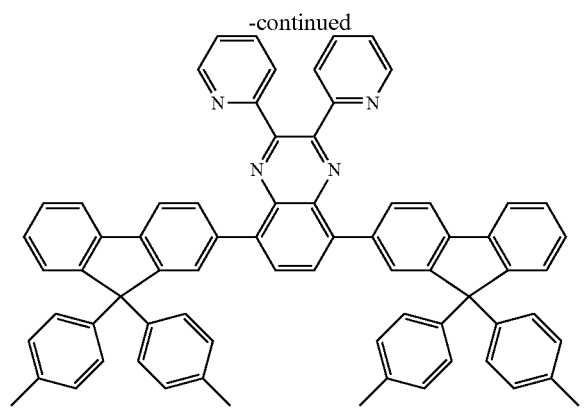

NE4
Chemical Formula: $C_{72}H_{52}N_4$
Molecular Weight: 973.21

13.6 g of benzothiadiazole (100 mmol) (compound 1) and 300 mL of HBr aqueous solution (48%) were added to a 1,000 mL round-bottom flask and heated to reflux. 15.4 mL of bromine (300 mmol) was then slowly dropped and reacted overnight. After adding sodium thiosulfate aqueous solution to quench the reaction, the resulting solution was filtered. The filtered solid was then washed with acetone. Thus, 25.3 g of light ashen solid product (compound 2) was obtained, with a yield of 86%.

2.94 g of compound 2 (10 mmol), 150 mL of ethanol and 50 mL of THF were added to a 250 mL round-bottom flask and stirred for 10 minutes. 1.51 g of Sodium borohydride (10 mmol) was then added and heated to reflux. After reacting overnight, the resulting solution was filtered with a filter paper and extracted using ether and saturated saline. The organic layer was then collected. After removal of water of the collected solution by adding dry magnesium sulfate and concentrated by reducing the pressure, 2.4 g of white solid product (compound 3) was obtained, with a yield of 90%.

585 mg of compound 3 (2.2 mmol), 420 mg of compound 22 (2 mmol), a specific amount of p-toluenesulfonic acid monohydrate (p-TSA) and 20 mL of trichloromethane were added to a 50 mL two-necked flask and heated to reflux. After reacting for 12 hours, 20 mL of sodium bicarbonate aqueous solution was added to quench the reaction. The resulting solution was then extracted using 20 mL of dichloromethane for several times. The organic layer was then washed with saturated saline and collected. After removal of water of the collected solution by adding dry magnesium sulfate, filtered and concentrated by reducing the pressure, the concentrated results were re-precipitated by dropping methanol. Thus, 875 mg of light yellow solid product (compound 23) was obtained, with a yield of 90%.

4.7 g of compound 9 (9.5 mol), 2 g of compound 23 (4.5 mmol), 313 mg of Pd(PPh$_3$)$_4$ (0.27 mmol), 165 mg of P(t-Bu)$_3$ (0.81 mmol), 5.8 mL of K$_2$CO$_3$ (2M in H$_2$O, 11.7 mmol) and 80 mL of toluene were added to a 150 mL two-necked flask and heated to reflux for 24 hours. The resulting solution was then extracted using dichloromethane for several times. The organic layer was then washed with saturated saline and collected. After removal of water of the collected solution by adding dry magnesium sulfate, filtered and concentrated by reducing the pressure, the concentrated results were re-precipitated by dropping an equivalent amount of methanol. Thus, 2.69 g of white solid product (compound NE4) was obtained, with a yield of 61%.

EXAMPLE 10

Preparation of Compound NE5

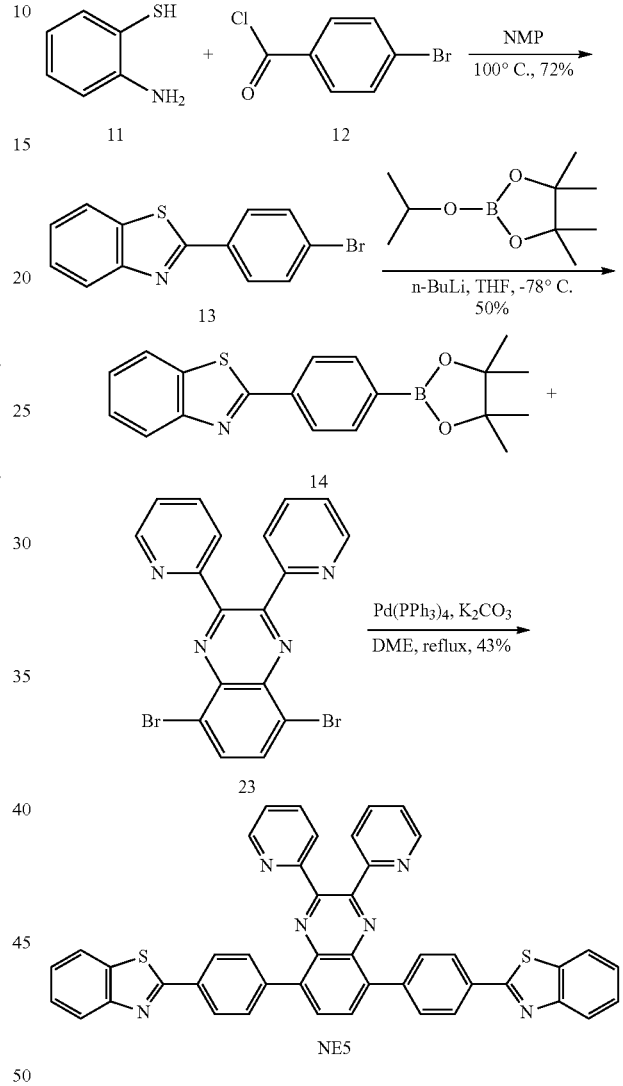

4.4 g of compound 12 (20 mmol), 50 mL of N-methyl-pyrrolidinone (NMP) and 2.1 mL of compound 11 (20 mmol) were added to a 250 mL two-necked flask and heated to 100° C. After one hour, the temperature was lowered to room temperature. Aqueous ammonia was then added to alkalize the resulting solution to the pH 8-9. After filtering and washing the filtered results with water, 4.1 g of white solid product (compound 13) was obtained, with a yield of 72%.

3.3 g of compound 13 (11.4 mmol) and 100 mL of dry THF were added to a 250 mL two-necked flask and cooled to −78° C. 10.7 mL of n-butyl lithium (1.6M, 17.1 mmole) was then added to react for 0.5 hour. 3.5 mL of 2-isopropoxy-4,4,5,5-tetramethyl-1,3,2-dioxaborolane (17.1 mmol) was then added at the same temperature of −78° C. After returning to room temperature and then reacting for 12 hours, the resulting solution was extracted using ethyl acetate and saturated saline. The organic layer was then collected. After removal of water of the collected solution by adding dry magnesium sulfate, filtered and concentrated by reducing the pressure, the concentrated results were re-crystallized using methanol. Thus, 1.9 g of white solid product (compound 14) was obtained, with a yield of 50%.

1.8 g of compound 14 (5.3 mmol), 1.1 g of compound 23 (2.4 mmol), 280 mg of Pd(PPh$_3$)$_4$ (0.24 mmol), 2.4 mL of K$_2$CO$_3$ (2M in H$_2$O) and 100 mL of DME were added to a 250 mL two-necked flask and heated to reflux for 18 hours. After the reaction was completed, the resulting solution was lowered to room temperature and concentrated by reducing the pressure to remove solvent. A great quantity of dark green precipitates was formed. The precipitates were then washed by water and methanol in order. Yellow-green solid was formed. The solid was purified by sublimation to form 2.1 g of yellow solid product (compound NE5) was obtained, with a yield of 58%.

EXAMPLE 11

Fabrication and Test of an Organic Light-Emitting Diode

First, an ITO glass substrate was provided to serve as an anode and washed with a cleaning agent and deionized water. After drying, 4,4'-bis[N-(naphthyl)-N-phenyl-amino]biphenyl (NPB) was evaporated on the ITO glass substrate to form a hole transport layer with a thickness of 300 Å. Irppy3 and 4,4'-N,N'-dicarbazole-biphenyl (CBP) (6-7%) were then co-evaporated on the hole transport layer to form a light-emitting layer with a thickness of 300 Å. Next, bathocuproine (BCP) was evaporated on the light-emitting layer to form a hole blocking layer with a thickness of 50 Å or 100 Å. Optionally, Bphen was evaporated on the light-emitting layer to form a hole blocking layer with a thickness of 50 Å. Next, the disclosed compound C3 or C4 was evaporated on the hole blocking layer to form an electron transport layer with a thickness of 200 Å. Next, LiF was evaporated on the electron transport layer to form a buffer layer with a thickness of 5 Å. Optionally, a layer of tris(8-hydroxyquinoline)aluminum (III) (Alq$_3$) with a thickness of 50 Å was further evaporated between the electron transport layer and the buffer layer. Finally, Al was evaporated on the buffer layer to form a cathode with a thickness of 1,200 Å. Thus, completing fabrication of an organic light-emitting diode.

Compared to the organic light-emitting diode fabricated from the conventional electron transport material (Bphen), the disclosed organic light-emitting diode fabricated from the electron transport material composed of the quinoxaline derivative (compound C4) had higher luminescent efficiency. For example, the brightness of the disclosed organic light-emitting diode fabricated from the electron transport material composed of the quinoxaline derivative (compound C4) was maintained at close to 90% of the original brightness following 600 hours of test. However, the brightness of the organic light-emitting diode fabricated from the conventional electron transport material (Bphen) decayed to less than 80% of the original brightness following 600 hours of test. The results indicated that the disclosed electron transport material composed of the quinoxaline derivatives had higher thermal stability than the conventional Bphen electron transport material.

The maximum brightness, driving voltage, current efficiency and CIE of the disclosed organic light-emitting diodes (devices A to C) fabricated from the electron transport material composed of the quinoxaline derivatives (compound C3 and compound C4) and the organic light-emitting diode (devices D to E) fabricated from the conventional electron transport materials (Bphen and Alq$_3$) are shown in Table 1. To summarize, the device compositions are as follows:

Device A: NPB (300)/Irppy3: CBP (6-7%) (300)/BCP (50)/compound C3 (200)/Alq$_3$ (50)/LiF (5)/Al (1,200);

Device B: NPB (300)/Irppy3: CBP (6-7%) (300)/Bphen (50)/compound C3 (200)/Alq$_3$ (50)/LiF (5)/Al (1,200);

Device C: NPB (300)/Irppy3: CBP (6-7%) (300)/BCP (100)/compound C4 (200)/LiF (5)/Al (1,200);

Device D: NPB (300)/Irppy3: CBP (6-7%) (300)/Bphen (300)/LiF (5)/Al (1,200); and Device E: NPB (300)/Irppy3: CBP (6-7%) (300)/BCP (100)/Alq$_3$ (200)/LiF (5)/Al (1,200).

TABLE 1

| Devices | Maximum brightness (cd/m$^2$) | Driving voltage (V) | Current efficiency (cd/A) | CIE (x, y) |
|---|---|---|---|---|
| A | 57,190 | 3.5 | 34.9 | (0.32, 0.61) |
| B | 82,123 | 3.5 | 46.0 | (0.32, 0.62) |
| C | 56,763 | 3.5 | 32.6 | (0.32, 0.62) |
| D | 51,177 | 3.5 | 31.3 | (0.32, 0.61) |
| E | 69,580 | 4.0 | 24.6 | (0.32, 0.62) |

The results indicated that the disclosed organic light-emitting diodes fabricated from the electron transport material composed of the quinoxaline derivatives had superior maximum brightness and current efficiency when compared to the conventional organic light-emitting diodes.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A quinoxaline derivative, represented by Formula (I) or (II):

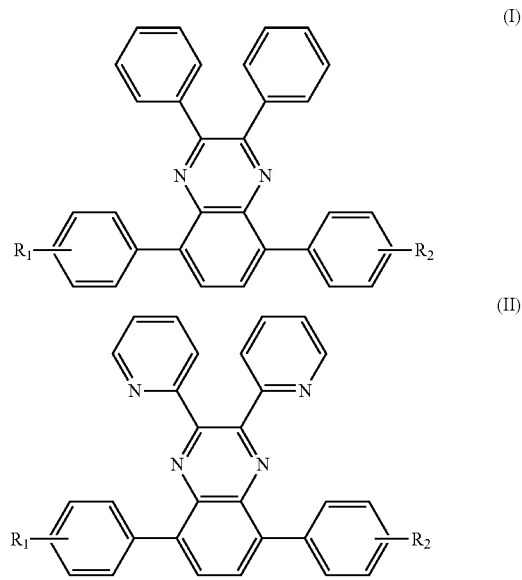

wherein
R₁ and R₂ in Formula (I) are, independently, halogen, methyl, ethyl, propyl, butyl or heteroaryl; and
R₁ and R₂ in Formula (II) are, independently, hydrogen, halogen, methyl, ethyl, propyl, butyl, aryl or heteroaryl.

2. The quinoxaline derivative as claimed in claim 1, wherein R₁ and R₂ are phenyl, furyl, thienyl, pyridyl, pyrimidyl, benzothiazolyl or benzoimidazolyl.

3. The quinoxaline derivative as claimed in claim 1, wherein the quinoxaline derivative comprises

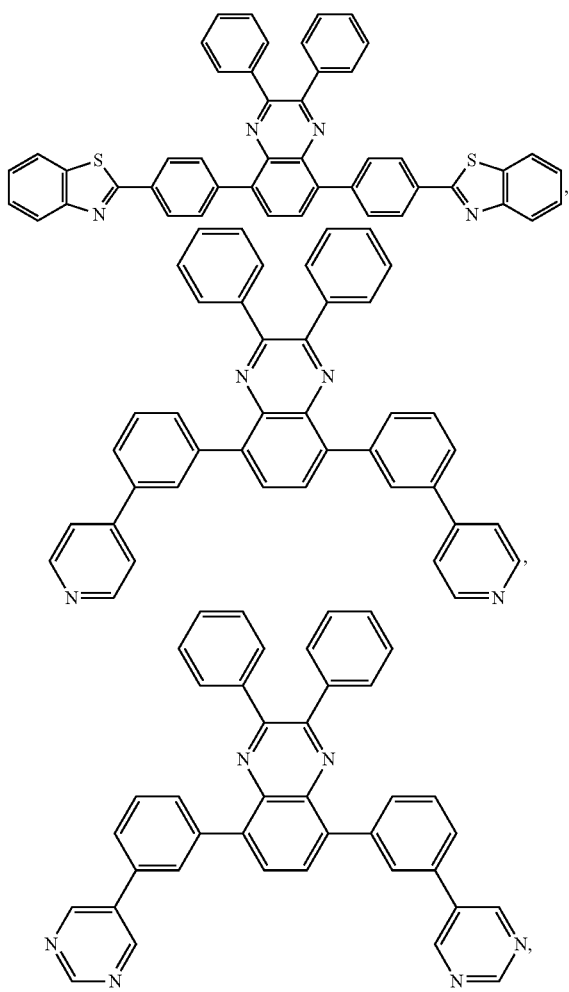

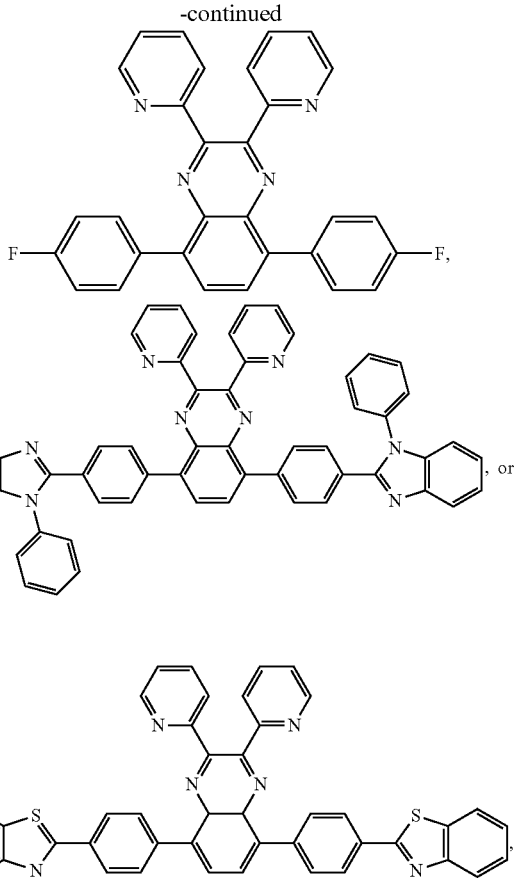

4. The quinoxaline derivative as claimed in claim 1, wherein the quinoxaline derivative is used as part of organic light-emitting diodes or organic solar cells.

5. An organic light-emitting diode, comprising:
a cathode and an anode;
a light-emitting layer disposed between the cathode and the anode; and
an electron transport layer comprising a quinoxaline derivative as claimed in claim 1, disposed between the light-emitting layer and the cathode.

\* \* \* \* \*